US00PP09846P

United States Patent [19]

Lommerse

[11] Patent Number: Plant 9,846

[45] Date of Patent: Apr. 1, 1997

[54] DAHLIA PLANT NAMED LIZZY

[76] Inventor: Henry C. J. Lommerse, P.O. Box 22, 1601 BM Enkhuizen, Netherlands

[21] Appl. No.: 260,451

[22] Filed: Jun. 14, 1994

[51] Int. Cl.[6] ..... A01H 5/00

[52] U.S. Cl. ..... Plt./87.8

[58] Field of Search ..... Plt./87.8

[56] References Cited

U.S. PATENT DOCUMENTS

P.P. 6,768 2/1989 Mulder ..... Plt./87.8

*Primary Examiner*—James R. Feyrer

*Attorney, Agent, or Firm*—Burns, Doane, Swecker & Mathis, L.L.P.

[57] ABSTRACT

A new and distinct cultivar of Dahlia plant named Lizzy characterized by its purple red ray floret color; full and dense inflorescences; large inflorescence diameter; inflorescences held above the foliage; compact growth habit; and simple leaf arrangement.

1 Drawing Sheet

The present invention relates to a new and distinct cultivar of Dahlia plant, botanically known as Dahlia cav., and hereinafter referred to by the cultivar name Lizzy.

Lizzy is a sport or mutation of the commercial Dahlia cultivar Connie, U.S. Plant Pat. No. 6,768. The plant of this disclosure was a spontaneous color mutation of unknown causation. I discovered the sport on Mar. 2, 1990 in a controlled environment facility in Enkhuizen, The Netherlands.

Asexual reproduction of the new cultivar by terminal cuttings from side shoots taken by me at Enkhuizen, The Netherlands, has shown that the unique features of this new Dahlia are stabilized and are reproduced true to type in successive generations of asexual reproduction.

The following characteristics have been repeatedly observed and are determined to be the basic characteristics of Lizzy. These characteristics in combination distinguish the new Dahlia from both its parent variety and other cultivated Dahlias of this type as a new and distinct cultivar:

1. The ray floret color is purple red.
2. The inflorescences are fuller and more dense compared to the cultivars. This increase in fullness is a result of an increased number of rows of ray florets and an increased number of ray florets per inflorescence.
3. The inflorescence diameter is larger than other cultivars.
4. Inflorescences are held above the foliage.
5. Plants are compact in growth habit and are suited for potted plant culture.
6. Leaves are simple and not compound.

The cultivar Lizzy is most similar to its parent cultivar, the commercial Dahlia cultivar Connie, in its inflorescence form and plant habit. The cultivar Lizzy differs from the cultivar Connie in its purple red ray florets compared to bright orange-red ray floret color of Connie; fuller inflorescences as a result of more rows of ray florets per inflorescence; larger inflorescence diameter; and simple leaf arrangement compared to the compound or trifoliate arrangement of leaves on the cultivar Connie.

The accompanying colored photograph illustrates the overall appearance and inflorescence color of the new cultivar, showing the colors as true as it is reasonably possible to obtain in colored reproductions of this type. The photograph is a top view of a single flowering pot of Lizzy.

The new cultivar has not been observed under all possible environmental conditions. The phenotype may vary significantly with variations in environment such as temperature, light intensity and daylength. The following is a detailed description of my new cultivar based on plants produced under normal commercial practice in Enkhuizen, the Netherlands, in a glass-covered greenhouse with average day temperatures of 18° C. and average night temperatures of 16° C.

Color references are made to The Royal Horticultural Society Colour Chart except where general terms of ordinary dictionary signficance are used.

Classification:

A. *Botanical.*—*Dahlia cav.* cv Lizzy.

B. *Common.*—Dahlia.

C. *Commerical use.*—Potted plant. This plant is well adapted for use as a patio plant, as well as a bedding plant, which has been shown to be adapted to be readily asexually reproduced from either cuttings or from the tubers produced by the plant.

Parentage:

Sport of commercial Dahlia cultivar Connie, U.S. Plant Pat. No. 6,768.

Propagation:

A. *Type.*—Terminal cuttings from side shoots or by tuberous divisions.

B. *Time to initiate roots.*—7 to 10 days at soil temperatures of 18° to 20° C.

C. *Rooting habit.*—Central root with numerous secondary roots.

Tuber description:

A. *Early or initial root system on rotted cuttings.*—Compact primary root having several compact secondary roots originating from the pericycle.

B. *Mature root system.*—Typical of the species, with maturity crown intiates are formed at the proximal end from which subsequent year's growth may develop in the form of aerial shoots.

Plant description:

A. *General appearance.*—Generally round in appearance.

B. *Plant size.*—Approximately 19 to 20 cm in height from top of soil level.

C. *Growth habit.*—Compact and upright.

D. *Foliage description.*—1. Leaf arrangement: Simple. 2. Leaf shape: Ovate to rounded with acuminate tip. 3. Leaf margin: Serrated. 4. Leaf size: a. Length without pedicel: 7 cm. b. Width: 4 cm. c. Pedicel length: 3 cm. 5. Leaf texture: a. Young leaves: Some luster. b. Fully expanded leaves: dull. 6. Young leaf color: a. Top side: 138A. b. Under side: 138B. 7. Fully expanded leaf color: a. Top side: 137B. b. Under side: 137C. 8. Leaf vein color: 138A.

Flowering description:

A. *Inflorescence.*—Fully double, decorative peony flowering habit with 5 rows of ray florets.

B. *Natural flowering season.*—July to October in the northern hemisphere.

C. *Inflorescence orientation.*—Inflorescences are held at a 120° angle to the peduncle and approximately 3.5 cm above the foliage.

D. *Quantity of inflorescccences.*—In general, 5 to 8 fully developed inflorescences per plant are present at one time.

E. *Ray florets.*—1. Shape: Slightly cupped, rounded at tip, narrow. 2. Color: Purple red. a. When opening, top side: 59A. b. When opening, under side: 59B. c. Fully open, top side: 60A. d. Fully open, under side: 60B. e. Fading to: 59C. 3. Number or ray florets: An average of 75 per inflorescence. 4. Size of inflorescence: a. Diameter: 10 cm. b. Height: 3.5 cm.

F. *Reproductive organs.*—1. Stamens: a. Anther color: 1B. b. Pollen color: 13C. 2. Pistils: a. Stigma shape: Narrow, lancet-shaped. b. Stigma color: 2B. c. Style color: 2C. d. Ovary number: single. e. Ovary size: 1 mm. f. Ovary color: 144A. g. Fertility: about the same as the parent plant.

Disease resistance: No suspectibility or resistance to fungal, bacterial or viral pathogens has been noted.

I claim:

1. A new and distinct cultivar of Dahlia plant named Lizzy, as illustrated and described.

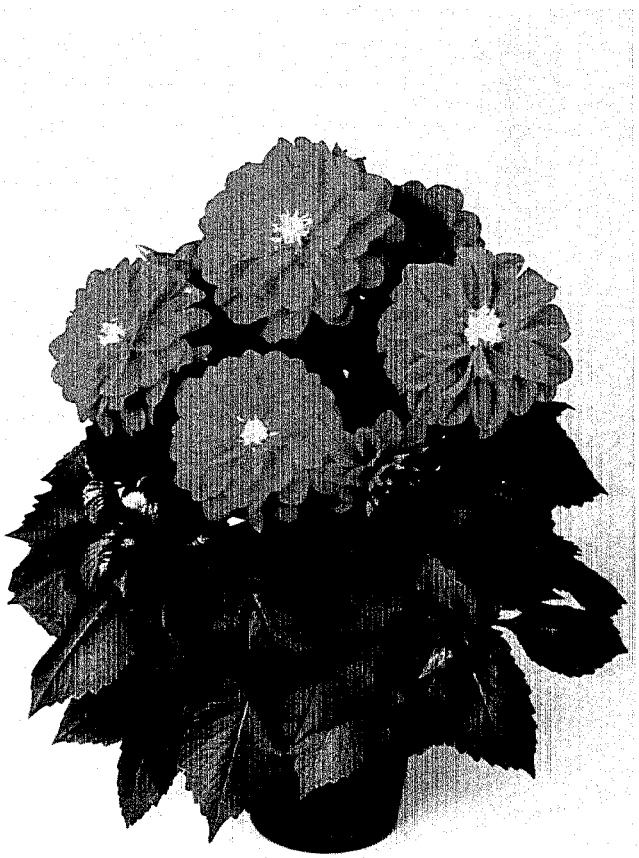

* * * * *